United States Patent
Hodge et al.

(10) Patent No.: US 8,961,576 B2
(45) Date of Patent: Feb. 24, 2015

(54) INTERNAL JOINT BRACING SYSTEM AND SUTURE ANCHORING ASSEMBLY THEREFORE

(75) Inventors: W. Andrew Hodge, Jupiter, FL (US); Slobodan Tepic, Zurich (CH); Stephen Bresina, Davos Dorf (CH)

(73) Assignee: Advanced Bone Anchor, LLC, Jupiter, FL (US)

( * ) Notice: Subject to any disclaimer, the term of this patent is extended or adjusted under 35 U.S.C. 154(b) by 0 days.

(21) Appl. No.: 13/274,565

(22) Filed: Oct. 17, 2011

(65) Prior Publication Data

US 2012/0035671 A1 Feb. 9, 2012

(51) Int. Cl.
*A61B 17/84* (2006.01)
*A61B 17/04* (2006.01)
*A61B 17/86* (2006.01)

(52) U.S. Cl.
CPC ......... *A61B 17/0401* (2013.01); *A61B 17/8625* (2013.01); *A61B 17/864* (2013.01); *A61B 17/8685* (2013.01); *A61B 2017/0414* (2013.01); *A61B 2017/0417* (2013.01); *A61B 2017/045* (2013.01); *A61B 2017/0462* (2013.01)
USPC .......................................... 606/328; 606/232

(58) Field of Classification Search
USPC ........................................... 606/74, 232, 328
See application file for complete search history.

(56) References Cited

U.S. PATENT DOCUMENTS

| | | | | |
|---|---|---|---|---|
| 5,129,902 A * | 7/1992 | Goble et al. | ...................... | 606/65 |
| 5,702,397 A * | 12/1997 | Goble et al. | ................... | 606/232 |
| 5,824,079 A * | 10/1998 | Siegler et al. | ................... | 128/898 |
| 5,891,168 A * | 4/1999 | Thal | ................................ | 606/232 |
| 5,931,840 A * | 8/1999 | Goble et al. | ..................... | 606/916 |
| 6,099,568 A * | 8/2000 | Simonian et al. | ............ | 623/13.11 |
| 6,368,326 B1 * | 4/2002 | Dakin et al. | ...................... | 606/103 |
| 6,818,010 B2 * | 11/2004 | Eichhorn et al. | ................ | 606/232 |
| 7,285,121 B2 * | 10/2007 | Braun et al. | ..................... | 606/279 |
| 7,322,978 B2 * | 1/2008 | West, Jr. | ........................... | 606/60 |
| 8,088,130 B2 * | 1/2012 | Kaiser et al. | .................... | 606/139 |
| 8,100,942 B1 * | 1/2012 | Green et al. | .................... | 606/232 |
| 8,313,509 B2 * | 11/2012 | Kostrzewski | .................. | 606/232 |
| 8,551,140 B2 * | 10/2013 | Denham et al. | ................ | 606/232 |
| 2002/0111653 A1 * | 8/2002 | Foerster | .......................... | 606/232 |
| 2002/0120270 A1 * | 8/2002 | Trieu et al. | ....................... | 606/61 |
| 2005/0277985 A1 * | 12/2005 | Wert et al. | ....................... | 606/228 |
| 2007/0118132 A1 * | 5/2007 | Culbert et al. | ................... | 606/72 |
| 2007/0203498 A1 * | 8/2007 | Gerber et al. | .................... | 606/72 |
| 2008/0065114 A1 * | 3/2008 | Stone et al. | ..................... | 606/139 |
| 2008/0306511 A1 * | 12/2008 | Cooper et al. | ................. | 606/232 |
| 2008/0312689 A1 * | 12/2008 | Denham et al. | ................ | 606/232 |
| 2008/0319478 A1 * | 12/2008 | Foerster et al. | ................ | 606/232 |
| 2009/0318966 A1 * | 12/2009 | Green et al. | .................... | 606/232 |

* cited by examiner

*Primary Examiner* — Christian Sevilla
(74) *Attorney, Agent, or Firm* — Keller Life Science; Michael J. Keller

(57) ABSTRACT

An internal bracing system is disclosed for stabilizing a joint such as the knee, shoulder, ankle or the like. The internal bracing system includes an extra-articular tension band mechanism and an anchor assembly therefore. The internal bracing system adds substantial control to unstable joints which is effective in limiting the pathological joint motions and internal slippage. The anchor anchoring assembly designed to affix a tethering device to various bony structures which form a joint, for the purpose of providing stability. The anchor assembly includes an anchor and a set screw. A double helix thread/chamber structure between the anchor and set screw securely holds the tether without binding.

7 Claims, 5 Drawing Sheets

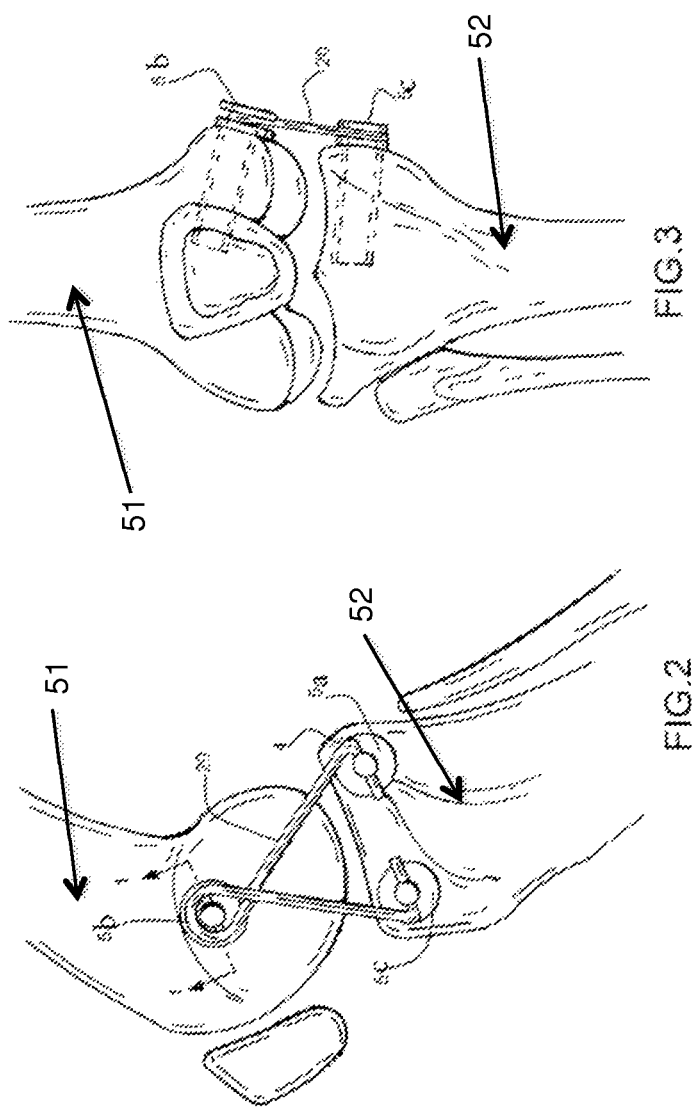

INTERNAL JOINT BRACING SYSTEM AND SUTURE ANCHORING ASSEMBLY THEREFORE

This application claims benefit of priority under 35. U.S.C. §119(e) of PCT application PCT/US10/31532 filed on Apr. 18, 2010, which claims priority to U.S. provisional patent application 61/170,446 filed on Apr. 17, 2009, the contents of which are expressly incorporated herein by reference. U.S. patent application Ser. No. 12/763,179 is incorporated by reference. The contents of all references cited herein are expressly incorporated by reference.

BACKGROUND OF THE INVENTION

1. Field of the Invention

This invention is generally directed toward an internal bracing system for the knee, shoulder, ankle or the like. The internal bracing system is designed to be located on the medial, lateral, anterior, or posterior aspect of the joint in a manner effective to control excessive laxity or traumatic rotatory and/or translational instability of the joint. The invention is more particularly directed toward an internal bracing system having an extra-articular tension band mechanism and anchoring assembly. The anchoring assembly is designed to affix a tethering device to various bony structures which form a joint.

2. Discussion of Related Art

It has been observed that subsequent to specific joint instabilities after ligament injury, trauma or chronic laxity (which can be more common in certain populations with high demands and genetic pre-disposition); there is a need for specialized internal bracing or ligament augmenters. Specifically, as seen in these populations, there can be severe combined ligament insufficiency and/or deficiencies leading to instability of the joint causing early progressive joint wear, arthritis, pain and dysfunction.

Existing externally worn joint braces have been used for years but have been uncomfortable and ineffective in providing the type of control and stability needed to control pathologic sequele of an unstable joint. The other traditional option of intra-articular ligament replacements are complex to install, have high failure rates and are generally not effective over time. Thus, there has been a general failure of external brace capacity and surgical intracapsular (complex positioning required) ligament reconstructions to control the high joint functional demands, e.g. control of the unstable motion and/or joint slippage or control the buckling or subluxation at high speed/stress motions causing the joint to still give away.

As a result of these observations, the present inventors have sought to restabilize the effected joints, by providing to these stretched or torn ligaments, augmenting or reinforcing structures, for example to extra capsular knee structures, thereby providing an 'internal bracing' like structure which can be surgically created by a simple, low-cost technique. This robust extra-capsular augment or internal bracing of the joint controls stability using simple artificial reinforcers or tension bands. This is done through this invention's ability to control the articular position of the particular joint allowing this to return to a more normal motion, while simultaneously limiting the abnormal translations and rotations, and thereby lessening abnormal stresses.

SUMMARY OF THE INVENTION

The present invention adds substantial control to unstable human joints through an 'internal bracing' extra-capsular approach which is effective in limiting the pathologic joint motions and internal slippage which leads to the pathologic, destructive unstable motions and high stresses seen commonly post-trauma and in cultures with genetic laxity and/or high demand knee performance, e.g. such as high stretch states where the ligaments are permanently loosened, lengthened or torn. By adding this 'internal brace' control it is expected to prevent or slow progression of arthritic wear, pain and instability of the joints in these individuals.

These artificial ligament anchors allow for fixation across a joint from bone to bone, while permitting the tether to move through a range of positions without damaging the tether at the anchor interface.

The 'internal brace' can be positioned as required to augment dysfunctional ligaments of the unstable joint as needed for good function. Multiple anchors can be used and the position of the anchors can be confirmed with a trialing template and fluoroscopic control, which will make the technique even simpler.

This robust extra-capsular augment or 'internal brace' of the joint controls stability using simple artificial reinforcers or tension bands. This is done through the invention's ability to control the articular position of the particular joint allowing this to return to a more normal motion at the same time limit the abnormal translations and rotations which lessen abnormal stresses.

Accordingly, it is a primary objective of the instant invention to provide an 'internal bracing' concept which allows for high function activities while controlling the damaging, pathological instability or slippage seen in patients with all type of joint dysfunction. It is a further objective of the invention to provide a system for more easily surgically tacking these ligament augments in place therefore allowing a wide range of generalized, less specialized surgeons to effectively use this technology.

It is yet an additional objective to provide a novel screw anchor with a central set screw made from biocompatible, high strength materials and incorporating a synthetic or biologic tether to be securely anchored to bone.

It is a still further objective to provide a method for attaching the tether to the anchor which dynamic movement of the tether without high risk of failure of the tether, thereby providing a unique construct which can utilize large radii bending, universal joints, and/or tensioners.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 is a top view illustrating an internal bracing system according to an embodiment of the present invention connected to a knee joint;

FIG. 3 is a side view illustrating the internal bracing system of FIG. 2;

DETAILED DESCRIPTION

The invention will now be more specifically described with reference to the aforementioned FIGS. 1-10.

Figure 10:
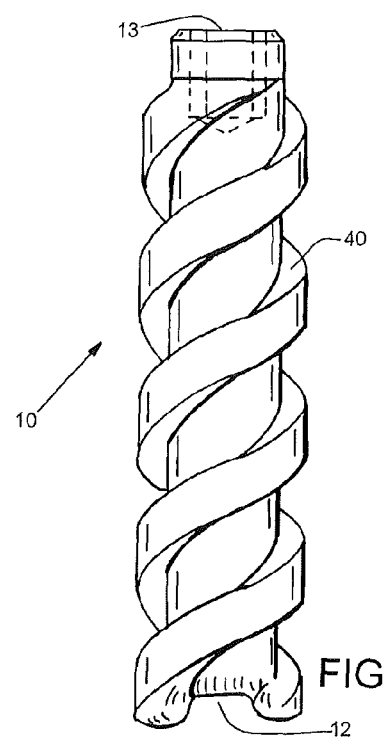
FIG. 10 is a side view of a set screw according to an embodiment of the present invention.

In accordance with an embodiment of the present invention a novel anchor assembly 1 is securely anchored to bone to attach a synthetic or biologic tether or suture 20. (Tether and suture are used interchangably herein to refer to the material attached to the bone anchor assembly for forming an internal bracing system according to an embodiment of the present invention.) The anchor assembly 1 includes an anchor member 5 and a central set screw 10. The anchor member 5 and set screw 10 are made from biocompatible, high strength materials. Details of the anchor member 5 are illustrated in FIGS. 4-9. Details of the central set screw 10 are illustrated in FIG. 10. The tether 20 is connected to the anchor assembly 1 through interaction of the anchor member 5 and the set screw 10. The attachment of the tether 20 allows dynamic movement of the tether 20 without high risk of failure of the tether. This unique construct can utilize large radii bending, universal joints, and/or tensioners. The locking of the tether 20 to the anchor assembly 1 is achieved by a novel design of the head of anchor member 5, interior plug 14 therein, and the set screw 10. The locking is performed in such a manner that the strength of the tether is not compromised.

The surface geometry and/or coating of the anchor member 5 permits a torsionally stable fixation to bone and allows good bony on-growth. The anchor 5 is designed to be pushed, e.g. hammered, into place in the bone. It has a cylindrical body 6 and a wider cylindrical head 7. Finistrated surface structures 30 extend longitudinally along the outer surface of the cylindrical body 6 at various locations around the periphery. The finistrated surface structures 30 provide torsional stability to the anchor member 5. Alternatively, the outer surface of the cylindrical body 6 could include threads (not shown) so that the anchor member 5 could be screwed into the bone. However, the pushed in anchor member is deemed preferable since screwing in of the anchor would likely require right and left hand screw threads depending on direction of force on the tether. The risk of using the wrong screw—resulting in failure to maintain tension of the tether—is thus eliminated by the preferred construction.

The head 7 has a cylindrical channel 21 narrower than the top 12a and bottom 12b thereof. A slot 4 is formed across the head. The slot extends to the level of the bottom 12b of the head. The channel 21 and slot 4 operate to retain and guide the tether into the center of the anchor member 5.

A bore 8 extends along the central axis of the head 7 and body 6 of the anchor member 5. A double helix thread/channel structure 9 extends along the interior of the bore 8. The double helix thread/channel structure ends before the bottom of the bore. A plug 14 is positioned in the bottom of the bore 8 at the end of the double helix thread/channel structure 9.

Preferably, the anchor member 5 is formed of Commercial Pure Titanium CP4 Ti, a titanium alloy, or a suitable polymeric material. The body 6 could also be hydroxyapatite coated (HA coating) to enhance bone ongrowth. If high strength is a requirement for the anchor, Ti alloy material should be used. The surface of body 6 of anchor member 5 is preferably rough blasted with Ra of approximately 5 for good bone ongrowth. The head 7 of anchor is preferably polished so no rough edges interface against the tether material. The plug 14 at bottom of bore 8 should be a biocompatible elastomeric material, e.g. a polyurethane, which material is generally available in different grades of hardness. The material for the plug 14 and hardness should be selected to impede rotation of the set screw 10, as discussed below.

The set screw 10 has a cylindrical construction with a double helix thread/channel structure 40 around the periphery thereof. The double helix thread/channel structure 40 mates with the similar structure in the interior of the bore 8 of the anchor member 5. The relationship between the double helix thread/channel structure 40 of the set screw 10 and the double helix thread/channel structure 9 of the anchor member 5 leaves space between the set screw and bore of the anchor member 5 to receive and retain the tether. One end of the set screw 10 includes a recess 12 to receive the tether. The other end of the set screw 10 has a hexagonal bore 13. The hexagonal bore 13 can receive a tool for rotating the set screw 10 to insert it into the anchor member 5. Of course, another mechanism, such as a Torx bore or slot for a screwdriver, could be used to rotate the set screw 10 for insertion.

Preferably the set screw is made from Ti Alloy Ti6A14V (Ti-Aluminum-Vanadium) or Ti6A17Nb (TAN Ti-Aluminum-Niobium) or a suitable polymeric material, e.g. PEEK. Preferably, the set screw has a smooth surface finish.

Figure 1:
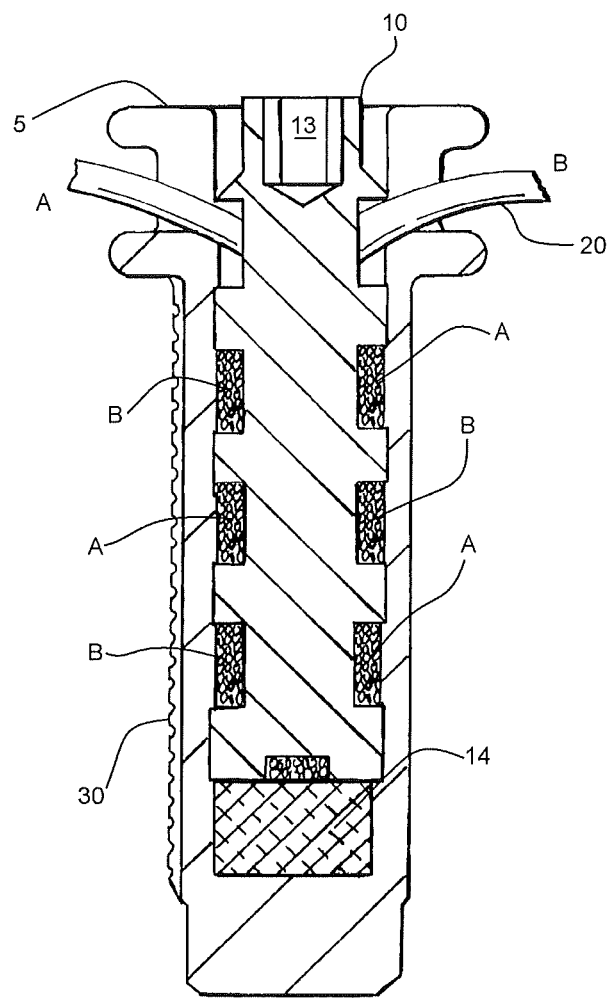
FIG. 1 is a partial section view, taken along lines 1-1 of FIG. 2, illustrating a suture anchoring assembly according to an embodiment of the present invention.
Figure 4:
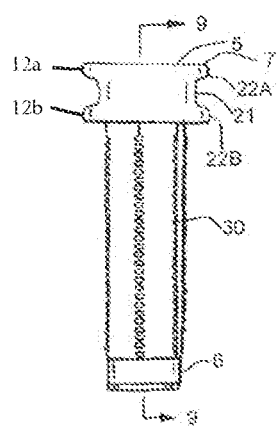
FIG. 4 is a side view of an anchor member according to an embodiment of the present invention.
Figure 7:
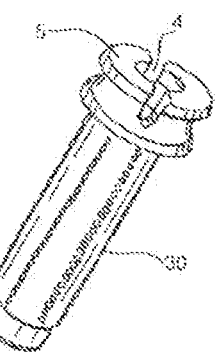
FIG. 7 is a perspective view of the anchoring member illustrated in FIG. 4.
Figure 5:
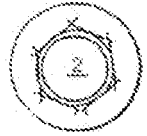
FIG. 5 is a bottom view of the anchor member illustrated in FIG. 4.
Figure 6:
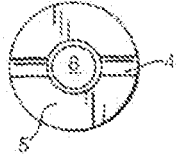
FIG. 6 is a top view of the anchor member illustrated in FIG. 4.
Figure 8:
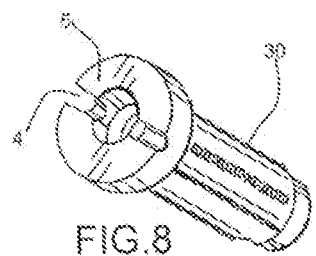
FIG. 8 is a perspective view of the anchoring member illustrated in FIG. 4.
Figure 9:
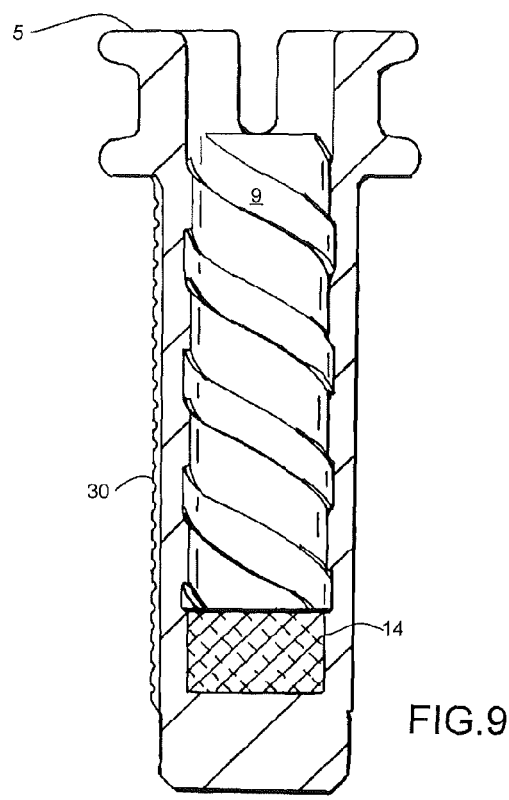
FIG. 9 is a section view taken along lines 9-9 of FIG. 4.

To attach the tether to the anchor assembly 1, the tether 20 is located in the recess 12 of the set screw 10. As the set screw 10 is threaded into the bore 8 of the anchor member 5, the tether 20 is guided into the double helix channel such that one leg of the tether is guided into one helix while the second leg is guided into the second helix of the set screw 10. Referring to FIG. 1, letter designations "A" and "B" reference the first and second legs of the tether 20 as it follows the double helix construction 40. As the set screw 10 is tightened to the bottom of the bore 8, the plug 14 compresses the tether 20 against the end of the set screw 10 and maintains force against the set screw 10 so that the set screw 10 is locked and prevented from rotating. The path of the tether 20 around the head 7 of the anchor member 5 and into the set screw 10, along with the wrapping through the channel in the set screw provide a gradual transfer of force from the tether to the anchor. By the time the tether 20 at the recess 12 of the set screw 10 is compressed by the plug 14 at the bottom of the anchor, the load remaining in the tether 20 is minimized. This allows for locking of the tether without knots. Knots cause sutures (tethers) to bend around corners of very small radii which cause high strains and early failure of sutures.

Additional features to prevent loss of strength of the tether at the anchor are the make-up of the tether and the radii and the shape of the path for the tether to be locked into. The tether material has high axial strength and high axial stiffness and may be either synthetic, biologic or hybrid. The radii of the path of the tether in the screw/plug and the set screw are made as large as possible to minimize strain in the individual filaments of the tether. By correct positioning of two, three or more 'internal ligaments' and adjusting of the tether, the internal brace construct can provide augmentation to almost any joint ligament. A simple jig (not shown) can be used for trial positions of the anchors to confirm the improved stability/function of the joint prior to final insertion of the anchors. This makes the surgery easy for a basic surgeon to perform. The function and position of the joint can be guided by navigation techniques of ultrasound or fluoroscopic imaging.

Various materials and configurations may be used as a tether in internal bracing system according to the present invention. Preferred fiber for use with the anchor assembly of the invention is that of oriented, high modulus, ultra high molecular weight polyethylene, such as DYNEEMA® from DSM, Netherlands, or SPECTRA® from Honeywell, USA. Preferred diameter of the fiber is between 10 and 20 micrometers, more preferably about 15 micrometers. Although any configuration of fibers is contemplated by the invention, in a preferred embodiment, fibers are left free from each other, as in yarn; e.g. neither diffusion bonding nor braiding is used in production. The anchor assembly of the present invention securely attaches to and holds all of the individual fibers in bundle. The use of free fibers prevents rubbing and stresses which can occur with braided or bonded fibers. The suture may be supplied with beaded ends, and secured/overmolded with low molecular weight poylyethylene. Other suitable fibers are polyesters, e.g. polyethylene terphthalate, polyamides, e.g. NYLON®, aramids, e.g. KEVLAR®, silk, biologics or the like. Resorbable fibers may also be used in certain applications, e.g. those based upon polylactic acid, polyglycolic acid, or polydioxanone.

In a preferred embodiment, the anchoring assembly 1 will be provided in the form of a kit. An exemplary kit might comprise an anchor kit and instrumentation kit, including the following:
- three sizes of anchors—S, M, L—each with a corresponding set screw;
- targeting template and trial jig for determining anchor position and allowing joint manipulation and control— envisioned method of control with radiograph, e.g. fluoro.
- drill guides in three different sizes, one for each anchor size.
- drill bits in three different sizes, one for each anchor size.
- anchor impactor rods in three different sizes, one for each anchor size.
- screw driver for set screws including three different sizes of Torx or hex drives with self retaining tips for securely holding the set screws.

Each size anchor and set screw can be color coded by anodizing, e.g. S—Brown, M—Blue, L—Green, for ease in matching sizes. Preferably, the anchor impact rods are designed to mate with the head 7 of the anchor member 5. The anchor impact rod would impact the top 12a of the head 7 of the anchor member 5, while a central extension at the front of the anchor impactor rod stabilizes the anchor member 5 onto the anchor impactor rod by seating in the bore 8.

Different sizes of anchor assemblies are necessary to accommodate different diameter tethers. The desired diameter tether will depend upon the use of the internal bracing system and the joints being supported. Approximate overall dimensions of the three different sizes for the anchor and set screw may be as follows (in mm):

|  | L | M | S |
|---|---|---|---|
| Anchor |  |  |  |
| Length | 30 | 25 | 20 |
| Bore Diam. | 8 | 7 | 6 |
| Head Diam | 11 | 10 | 8.5 |
| Set screw |  |  |  |
| Length | 20 | 16 | 12 |
| Diam. | 6 | 5 | 4.2 |
| Tether diam. | 2.0 | 1.6 | 1.25 |

The anchor assembly can be used for internal bracing of many different types of joints. To create an internal bracing system, two or more anchor assemblies are positioned at various locations in the joint as necessary to provide stability and allow proper movement of the joint. For example a first anchor 5a is placed in a first bone 52 and a second anchor 5b is placed in a second bone 51. Preferably a third anchor 5c is also placed in a first bone 52. A tether 20 passes through the first anchor 5a in the first bone 52 and is looped around the second anchor 5b in the second bone 51 and is terminated in a third anchor 5c in the first bone 52. In any internal bracing system, each end of the tether is attached to one of the anchor assemblies. The tether may be looped around one or more additional anchor members (with or without the set screw inserted therein), to provide the necessary stability and range of motion. Various configurations of internal bracing systems for different joints are disclosed herein. However, these bracing systems are merely representative of internal bracing systems which can be created using anchoring assemblies of the present invention.

Knee Joint Internal Bracing

This invention serves the purpose of adding substantial control to unstable human knee joint through an 'internal bracing' extra-capsular method limiting the pathologic joint motions and internal slippage which leads to the pathologic, destructive unstable motions which create high stresses and causes damage to the articular cartilage. These circumstances are seen commonly post-trauma and in cultures with genetic laxity and/or high demand knee performance, i.e. such as high stretch states where the ligaments are permanently loosened, lengthened or torn. By adding this 'internal brace' control it is expected that these high stresses will be partially prevented and the slow progression of arthritic wear, pain and instability of knee joints in these individuals.

Currently, when a knee becomes unstable, the first line of treatment could be an externally worn joint brace which have been used for many years but recently have been customized to the individual for better fit and function. Usually, these knee braces have been uncomfortable and ineffective in providing the type of control and stability needed to control pathologic sequelae of an unstable joint (ref: Hodge, Harman & Banks; J. of Arthroplasty; vol 24; #3, p 448; 2009). Surgical options have also existed for many years with intra-aricular ligament replacements and repairs which have used both biologic and artificial constructs. These procedures involve major surgery with opening the joint and primarily have involved restoring the cruciate ligaments which are complex to install and have high failure rates becoming ineffective over time.

This invention repairs knees with stretched or torn ligaments by augmenting and/or reinforcing these structures by an extra capsular tension band or internal brace configuration as illustrated in FIGS. 2 and 3. This becomes an easy to insert, low cost solution to instability of the knee joint through a percutaneous surgery which implants this 'internal bracing' or tension band like structure. This robust extra-capsular augment or 'internal brace' of the joint controls stability using these simple artificial, biologic or hybrid extra articular tension bands. This is done through this invention's ability to restore the articular stability of the knee joint allowing it to return to a more normal motions, limiting the abnormal translations and rotations which create high, abnormal stresses leading to joint damage and arthritis. The invention utilizes fiber materials made of strong synthetic, biologic or hybrid materials with slight elastic properties. It can be attached to one of several types of fixed, adjustable, pivoting, expandable screw anchors with a pulley mechanism and/or rotational platform plate. These bone anchors are firmly fixed in bone with a post device that avoids loosening and provides long-term biologic fixation. This device serves as the anchor for the single or double armed portion of the tension band which are attached by screws with or without a synthetic plate on the opposite side of the joint. Two or more anchor screws may be used in anterior, posterior, medial or lateral capsule of the knee.

Each knee joint will have a set of sized templates which identify the origins and insertions of the medial, lateral collateral ligaments or popliteal ligament which stabilize the joint. The template allows for temporary pinning of the location of the permanent anchors. Utilizing these, the extra-articular tension bands are attached to these temporary posts allowing the joint to be tested for stability while taken through a natural range of motion. Once the desired stability is obtained, the locations are marked and the permanent anchors are inserted for final trialing and tensioning.

For precise placement of actual knee joint internal bracing, fluoroscopic, radiographic, or ultrasonic analysis can provide an intra operative view with or without 3D animations looking at actual internal knee motions defining the active, dynamic function and efficacy of this new invention. This will demonstrate basic improvements in knee joint function and stability. Human joint kinematic testing of the knee joint stability will be performed post-op with high speed camera (Vicon) motion analysis before and after application of the 'Internal Brace.'

Femoral Patellar Internal Bracing

Figure 11:
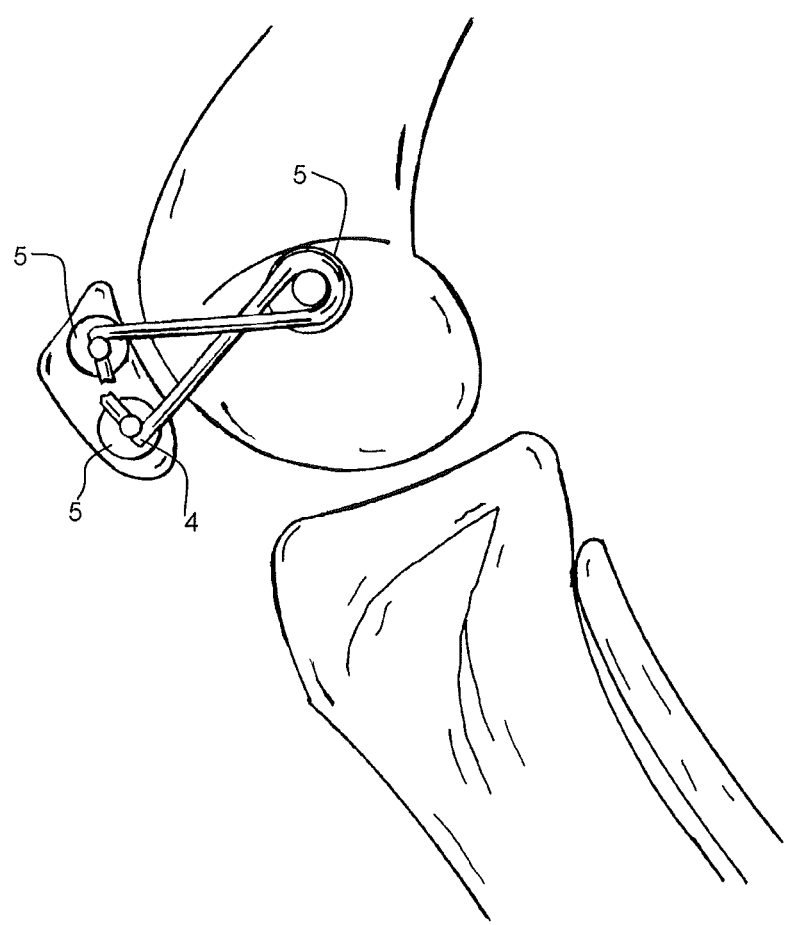
FIG. 11 is a top view illustrating an internal bracing system according to an embodiment of the present invention on a knee joint.

The femoral patellar join is one of the most unstable joints in the body. Sometimes this is do to injury but many times may relate to genetic ligament laxity or a congenitally shallow femoral patellar groove. The ligament that is most important in patellar stability is the medial patellar femoral Ligament complex (MPFL). With this new bone anchor/tension band system, this ligament can be recreated to give patellar stability and knee strength with reduced pain of mal tracking. The main bone anchor is place near the medial femoral epicondyle with two simple bone anchors in the patella creating a two pole recreation of the MPFL, as illustrated in FIG. 11.

Ankle Joint Internal Bracing

The ankle joint is the most injured and causes the most disability of any joint injury. This is primarily due to ankle sprains and strains which are due to ligament laxity and tears. As with the knee as stated above, the 'internal brace concept' works extremely well in the ankle providing needed stability. The ankle is a mortice type of joint that has mainly anterior, medial and lateral ligaments and any or all of these can become stretched or torn leading to high stresses and articular damage with arthritis. Some individuals have inherent laxity of these ligaments while others have chronic injuries to this joint.

The current treatments of these ankle instabilities are usually wearing a brace or high top shoe with reinforced strapping. These are cumbersome and uncomfortable so many times are only worn infrequently. As with the knee also, there are surgical methods of various types of ligament reinforcers and reconstruction mostly using nearby tendons which are harvested for application to usually medial or lateral aspects of the ankle joint. These operations diminish ankle function by removing one or more nearby tendons and have traditionally not held up over time because of stretching out or rupturing.

This invention takes unstable ankles with stretched or torn ligaments and augments and reinforces these structures with an extra capsular tension band or internal brace configuration. This becomes a simple, low cost solution to instability of the ankle joint with a percutaneous surgery which implants this 'internal bracing' or tension band like structure. This robust extra-capsular augment or 'internal brace' of the joint controls stability using these simple artificial, biologic or hybrid reinforcers or tension bands. This is done through this invention's ability to restore the articular position of the ankle joint allowing it to return to a more normal motions, limiting the abnormal translations and rotations which create high, abnormal stresses leading to joint damage and arthritis. The invention utilizes these extra-articular tension band mechanism made of strong synthetic, biologic or hybrid materials with slight elastic properties. It is attached to one of several types of fixed, adjustable, pivoting, expandable screw anchors with a pulley mechanism and/or rotational platform plate. These bone anchors are firmly fixed in bone with a post device that avoids loosening and provides long-term biologic fixation. This device serves as the anchor for the single or double armed portion of the tension band which are attached by screws with or without a synthetic plate on the opposite side of the joint. Two or more screws may be used in anterior, posterior, medial or lateral and can be associated with locking, capture inserts at the extremes of the plate.

The ankle joint has a set of templates which identify where the origins and insertions of the Deltoid medial collateral, lateral fibular collateral ligaments and anterior tibial talar ligament which provide the primary stability of the joint. The template allows for temporary pinning of the location of the permanent anchors. Utilizing these, the extra-articular tension bands are attached to these temporary posts allowing the joint to be tested for stability while taken through a natural range of motion. Once the desired stability is obtained, the locations are marked and the permanent anchors are inserted for final trialing and tensioning.

Human joint kinematic testing of the ankle joint stability will be performed with high speed camera (Vicon) motion analysis before and after application of the 'Internal Brace.' This will demonstrate basic improvements in ankle joint function and stability. For more precise measurements of actual ankle joint internal mechanics, fluoroscopic, radiographic, or ultrasonic analysis can provide an internal view and animations looking at actual internal ankle motions defining the active, dynamic function and efficacy of this new invention.

Spine Internal Bracing

The spine becomes unstable with advancing age and disease. The goals of modern spine surgery are to obtain stability while maintaining motion. This new invention allows 'internal bracing of the spine by setting up tension bands utilizing our novel bone anchoring system which allows rotations and translations of the spine while providing a stabilizing element. These tension bands can be anterior or lateral fixing to two adjacent vertebral bodies or can be posterior and go between spinous processes. These simple tension bands can be used in conjuction with implants such as artificial discs to provide the correct tension for these devices to remain stable.

Separated Shoulder Internal Bracing

When a shoulder is injured with so called 'separation' this refers to a disruption of the acromioclavicular joint and the coracoclavicular ligament. This can be difficult to repair, but with our new bone anchor/tension band system it is simplified. The bone anchor is placed in the distal clavicle while the tension band is wrapped around the coracoid process reconstructing the coracoclavicular ligament while the acromioclavicular joint heals or fibroses.

Wrist Internal Bracing

The dorsal radiocarpal ligaments are commonly injured and become unstable with age. These ligaments can now be reconstructed with our novel bone anchor tension banding system by placing one or more anchors in the distal radius and spaning the dorsal wrist joint to place other anchors in the proximal row of carpal bones. This provides an excellent 'internal bracing' mechanism restoring the patients grip strength and function.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An internal bracing system for a joint of a body comprising:
   a suture;
   a first bone anchor for positioning in a first bone of a joint;
   a second bone anchor positioned in a second bone of a joint;
   a third bone anchor for positioning in the first bone of a joint;
   wherein the suture connects the first bone anchor to the second bone anchor and connects the second bone anchor to the third bone anchor in a manner which stabilizes the joint;
   wherein each of the bone anchors comprises:
      an anchor member comprising a longitudinal threaded bore, an annular channel on a head for receiving the suture, a straight channel extending on a diameter of the head portion for receiving the suture and intersecting the annular channel at opposing ends of the annular channel, a plurality of longitudinal structures on a shaft, each of the longitudinal structures comprising a series of protrusions; and
      a set screw threadably insertable into the longitudinal threaded bore.

2. The internal bracing system according to claim 1 wherein the bone anchors are arranged to retain a portion of the suture.

3. The internal bracing system according to claim 1 wherein the at least one bone anchor includes a bone anchor assembly including:
   an anchor member having a central bore therein for insertion into the bone;
   a set screw insertable into the bore of the anchor member such that the suture is retained between the set screw and the bore of the anchor member when the set screw is inserted in the bore.

4. The internal bracing system according to claim 3 wherein the suture is formed of a high strength-high modulus fiber selected from a group comprising:
   oriented ultra high molecular weight polyethylenes, polyesters, polyamides, aramids, silk and biologics.

5. The internal bracing system according to claim 4, wherein the suture is formed of a plurality of fibers which are free of each other in the form of a bundle.

6. The internal bracing for human joints according to claim 1, wherein the joint is from the group comprising: a femorotibial joint, a patello-femoral joint, an ankle, an elbow, and a shoulder.

7. the internal bracing system of claim 1 where in the suture comprises ultra high molecular weight polyethylenes.

* * * * *

UNITED STATES PATENT AND TRADEMARK OFFICE
CERTIFICATE OF CORRECTION

| | | |
|---|---|---|
| PATENT NO. | : 8,961,576 B2 | Page 1 of 1 |
| APPLICATION NO. | : 13/274565 | |
| DATED | : February 24, 2015 | |
| INVENTOR(S) | : Hodge et al. | |

It is certified that error appears in the above-identified patent and that said Letters Patent is hereby corrected as shown below:

In the Specification

Col. 1 Line 5-12, should read

This application is a Continuation application of PCT International Application No. PCT/US10/31532 filed on April 18, 2010, which claims priority from U.S. Provisional Patent Application Serial No. 61/170,446 filed April 17, 2009, the contents of which are expressly incorporated herein by reference. U.S. Patent Application 12/763,179 is incorporated by reference. The contents of all references cited herein are expressly incorporated by reference.

Signed and Sealed this
Fourteenth Day of July, 2015

Michelle K. Lee
*Director of the United States Patent and Trademark Office*